(12) United States Patent
Piedras-Renteria et al.

(10) Patent No.: US 10,597,655 B2
(45) Date of Patent: *Mar. 24, 2020

(54) METHODS FOR MODULATING KLHL1 LEVELS, METHODS FOR MODULATING CURRENT ACTIVITY IN T-TYPE CALCIUM CHANNELS, MOLECULES THEREFOR, AND METHODS FOR IDENTIFYING MOLECULES THEREFOR

(71) Applicant: Loyola University Chicago, Maywood, IL (US)

(72) Inventors: Erika Sofia Piedras-Renteria, Riverside, IL (US); Jody Lee Martin, Oak Park, IL (US)

(73) Assignee: Loyola University Chicago, Maywood, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/887,228

(22) Filed: Feb. 2, 2018

(65) Prior Publication Data

US 2018/0273951 A1     Sep. 27, 2018

Related U.S. Application Data

(63) Continuation-in-part of application No. 15/273,079, filed on Sep. 22, 2016, now Pat. No. 10,047,377.

(60) Provisional application No. 62/221,960, filed on Sep. 22, 2015.

(51) Int. Cl.
   *C12N 15/113*   (2010.01)
   *C12N 15/86*    (2006.01)
   *C12Q 1/6876*   (2018.01)

(52) U.S. Cl.
   CPC ............ *C12N 15/113* (2013.01); *C12N 15/86* (2013.01); *C12Q 1/6876* (2013.01); *C12N 2310/51* (2013.01); *C12N 2310/531* (2013.01); *C12N 2330/51* (2013.01); *C12N 2750/14143* (2013.01); *C12Q 2600/136* (2013.01); *C12Q 2600/158* (2013.01)

(58) Field of Classification Search
None
See application file for complete search history.

(56) References Cited

U.S. PATENT DOCUMENTS

| | | | | |
|---|---|---|---|---|
| 2008/0113351 A1* | 5/2008 | Naito | ................... | A61K 31/713 435/6.11 |
| 2009/0217404 A1* | 8/2009 | Lowe | ................. | A01K 67/0271 800/18 |
| 2011/0230548 A1* | 9/2011 | Bot | ....................... | C12N 15/111 514/44 R |
| 2012/0260355 A1* | 10/2012 | Cohen | ................... | C12Q 1/6897 800/3 |
| 2013/0195801 A1* | 8/2013 | Gao | ....................... | C12N 15/86 424/93.2 |

OTHER PUBLICATIONS

Perissinotti et al. Cell Calcium vol. 55:269-280, Mar. 21, 2017.*
Mansha et al. Mol. Biol. Rep. vol. 39:10227-10234, 2012.*
Le Bec et al. Gene Therapy vol. 13:805-813, 2006.*

* cited by examiner

*Primary Examiner* — Sean McGarry
(74) *Attorney, Agent, or Firm* — Hartman Global IP Law; Gary M. Hartman; Domenica N. S. Hartman

(57) ABSTRACT

Methods for modulating T-type calcium channel activity without directly targeting the T-type calcium channels are provided that include modulating kelch-like protein 1 (KLHL1) levels in a subject by providing a small hairpin RNA (shRNA) that targets a KLHL1 gene, and then administering the shRNA to the subject in an amount sufficient to modulate KLHL1 gene expression. The KLHL1 level directly effects current activity in T-type calcium channels and therefore modulation of KLHL1 gene expression indirectly modulates current activity in T-type calcium channels. The methods may be implemented with, for example, an shRNA molecule suitable for modulating a KLHL1 level in the subject which may be provided as a plasmid encoding the shRNA molecule or an adeno-associated virus vector encoding the shRNA molecule. Methods of identifying compounds that modulate current activity in T-type calcium channels by determining an effect of the compound on KLHL1 gene expression are also provided.

8 Claims, 15 Drawing Sheets

Specification includes a Sequence Listing.

METHODS FOR MODULATING KLHL1 LEVELS, METHODS FOR MODULATING CURRENT ACTIVITY IN T-TYPE CALCIUM CHANNELS, MOLECULES THEREFOR, AND METHODS FOR IDENTIFYING MOLECULES THEREFOR

CROSS REFERENCE TO RELATED APPLICATIONS

This is a continuation-in-part patent application of co-pending U.S. patent application Ser. No. 15/273,079, filed Sep. 22, 2016, now U.S. Pat. No. 10,047,377, which claims the benefit of U.S. Provisional Application No. 62/221,960, filed Sep. 22, 2015. The contents of these prior applications are incorporated herein by reference.

SEQUENCE LISTING

The instant application contains a Sequence Listing which has been submitted electronically in ASCII format and is hereby incorporated by reference in its entirety. Said ASCII copy, created on May 22, 2018, is named B8-5106_SL.txt and is 927 bytes in size.

BACKGROUND OF THE INVENTION

The present invention generally relates to medical treatments. The invention particularly relates to modulating current activity in T-type calcium channels in a subject to treat pain and other conditions.

Transient opening ("T-type") calcium channels are low-voltage activated calcium channels that open during membrane depolarization. These channels aid in mediating calcium influx into cells and depolarizing the membrane in order to induce an action potential. They can also mediate calcium influx after an action potential or depolarizing signal. The entry of calcium into various cells has many different physiological responses associated with it. Within cardiac and smooth muscle cells, voltage-gated calcium channel activation directly initiates contraction by allowing the cytosolic calcium concentration to increase. In addition to their presence within cardiac and smooth muscle, T-type calcium channels are also known to be present in many neuronal cells within the central nervous system. T-type calcium channels are distinct from L-type (long-lasting) calcium channels as T-type channels are activated by more negative membrane potentials (low voltage-activated, LVA), have small single channel conductance, and are generally unresponsive to conventional calcium antagonist drugs directed to L-type calcium channels. These distinct calcium channels are generally located within the brain, peripheral nervous system, heart, smooth muscle, bone, and endocrine system.

There are several lines of evidence that support the claim that T-type channel modulation has an effect on pain sensation. Overall, when neuronal excitability is low, T-type currents are activated to increase excitability. These channels are encoded for by different genes; CACNA1G, CACNA1H, and CACNA1I, which encode for the principal T-type channel subunits alpha1G, alpha1H and alpha1I. These genes are expressed in neurons, however, they are not usually expressed at the same levels. For instance, alpha1G and alpha1H T-type calcium channel expression is higher in the back of the spinal cord, and alpha1G is more abundant than alpha1H in thalamocortical relay neurons. In dorsal root ganglia (DRG) in the peripheral nerves, alpha1H function is related to hyperalgesic reaction against thermo-stimuli or mechanical stimuli and recent results strongly implicate T-channels in the processing of nociceptive signals in both the peripheral and central nervous systems. It is known that in-vivo silencing of the CaV3.2 T-type calcium channels in sensory neurons results in antiallodynic and analgesic effects in rat models of both acute thermal and mechanical pain. Local injection of CaV3.2 antisense oligonucleotides also causes significant and long-term attenuation of induced neuropathic hypersensitivity. CACNA1H T-type channel KO mice exhibit attenuated responses to mechanical, thermal, and chemical cutaneous pain stimuli and chemical visceral pain stimuli.

Most conventional methods for modulating T-type channel activity are performed by administering drugs that generally include a T-type calcium channel inhibitor as an effective ingredient. Usually, these drugs are modifications of already known channel blockers. For example, mibefradil is a drug that targets T-type channels, but unfortunately also affects other types of channels as well, such as high voltage-activated (HVA) channels. As such, it has currently been withdrawn from commercial sale apparently due to its undesirable side effects and drug interactions.

Conventional methods and drugs target T-type channels directly for the treatment of pain. A major problem of this approach is that T-type channels are present in most excitable cells, including neurons and cardiac cells. Therefore, their direct targeting can cause unwanted side effects, some of which may be lethal. Similarly, available chemicals that target T-type channels are not selective, and can also affect other types of channels, for example HVA channels, with serious consequences.

Accordingly, there is a desire for methods and compounds capable of modulating T-type channel activity that avoids these adverse side effects.

BRIEF DESCRIPTION OF THE INVENTION

The present invention provides methods and compounds suitable for modulating T-type calcium channel activity without directly targeting the T-type calcium channels. The present invention also provides methods of identifying such compounds.

According to one aspect of the invention, a method is provided for modulating a kelch-like protein 1 (KLHL1) level in a subject by providing at least one small hairpin RNA sequence (shRNA) that targets a KLHL1 gene, and then administering the shRNA to the subject in an amount sufficient to modulate KLHL1 gene expression.

According to another aspect of the invention, a method of modulating current activity in T-type calcium channels in a subject includes providing at least one small hairpin RNA sequence (shRNA) that targets a kelch-like protein 1 (KLHL1) gene and administering the shRNA sequence to the subject in an amount sufficient to modulate KLHL1 gene expression, wherein the KLHL1 level directly alters current activity in T-type calcium channels.

According to yet another aspect of the invention, a method of identifying a compound that modulates current activity in T-type calcium channels includes determining an effect of the compound on KLHL1 gene expression and identifying the compound as a T-type calcium channel modulator based on the determined effect.

Other aspects of the invention include shRNA molecules suitable for modulating a KLHL1 level in a subject, a plasmid encoding the shRNA molecule, and an adeno-associated virus vector encoding the shRNA molecule.

Technical effects of the methods described above include the ability to indirectly modulate current activity in T-type calcium channels by controlling the KLHL1 level in a subject, thereby avoiding certain adverse side effects that have been associated with compounds that directly target T-type calcium channels.

Other aspects and advantages of this invention will be further appreciated from the following detailed description.

BRIEF DESCRIPTION OF THE DRAWINGS

FIG. 1A represents example western blots. FIG. 1B represents summary data showing that alpha 1H protein levels were decreased in DRG tissue from KO mice. Experimental n is stated in parenthesis.

FIG. 2A represents examples of electrophysiology experiments from WT and KO DRGs, obtained from a holding potential (Hp)=−90 mV and showing all calcium current components present in the DRG neurons: high-voltage and low-voltage activated or T-type currents. FIG. 2B represents the T-type current component subtraction. Traces obtained at Hp=−50 mV are subtracted from those obtained at −90 mV, providing the T-type current contribution. FIG. 2C represents summary data showing I-V curves from Hp=−90 mV. The asterisk indicates the peak voltage for T-type currents, which is significantly different in WT vs. KO. FIG. 2D represents the T-type current I-V curve obtained as described in panel B (peak at −30 mV) in WT and KO neurons.

FIG. 3A represents example traces obtained with the ramp protocol shown in the middle of the panel. FIG. 3B represents summary data showing that the rheobase, or the minimum current necessary to elicit the first action potential, is increased in the KO, indicating decreased excitability.

FIG. 4A schematically represents use of a Von Fey filament to measure paw withdrawal time on a mouse. FIG. 4B depicts the 50% threshold values (calculated as described in Chaplan, 1994). Significance was tested with Student's T-test. FIG. 4C represents the same data as FIG. 4B, showing withdrawal responses of wild-type and KO mice plotted in seconds as a function of filament pressure applied. Significance was tested with Student's T-test. FIG. 4D shows the same data plotted as cumulative distribution to obtain the 50% withdrawal response of the mouse populations. Significance was tested using non-parametric analysis (Komogorov-Smimov).

FIGS. 7-12 represent the individual analysis at three different viral titers. FIGS. 7-10 show that two of the lower titers tested (4.4×1010 and 5.1×1010 virus, respectively) did not achieve significance. FIG. 11-12 depict the data obtained with 9×10^10 virus, which induced lower pain sensitivity (increased 50% withdrawal threshold) in mice paws injected with shKLHL1 compared to control virus injections.

DETAILED DESCRIPTION OF THE INVENTION

The present invention generally relates to modulation of kelch-like protein 1 (KLHL1) levels in subjects, including but not limited to humans. The KLHL1 belongs to a family of actin-organizing proteins related to *Drosophila* Kelch. Investigations leading to the present invention determined that KLHL1 is a calcium channel modulator. Specific results of these investigations indicated that short-term down-regulation of KLHL1 using shKLHL1 adenoviral delivery to hippocampal neurons in vitro resulted in down regulation of CACAN1H T-type currents, and long-term down-regulation of KLHL1 in vivo in KLHL1 knock-out (KO) mice models caused changes in T-type current activity and expression depending on the tissue, with varying degrees of homeostatic compensation. Another of these investigations determined that DRG neurons from KO KLHL1 mice had decreased expression of alpha1H T-type channels, decreased T-type current density, decreased excitability, and decreased mechanical sensitivity. Specifically, the knockout of KLHL1 resulted in a 30% reduction of T-type channel activity and an increase in the paw-withdrawal time of 50% of the mice population from 4.9 seconds in wild-type mice to 7.3 seconds in knockout mice (i.e., ~50% decrease in threshold). Similar results are evidenced by FIGS. 1A, 1B, 2A-2D, 3A, 3B, and 4A-4D.

In summary, these investigations indicated that modulation of KLHL1 levels has an effect on pain sensation and sensitivity through an effect on T-type calcium channel activity. As such, certain aspects of the present invention generally relate to methods for modulating KLHL1 levels to control membrane excitability to treat pain and other conditions, such as but not limited to those conventionally treated with T-type calcium channel inhibitors. Further aspects of the invention include pharmaceuticals comprising a KLHL1 modulator for treating pain and other conditions, and methods of screening for such pharmaceuticals by investigating the modulation of KLHL1 gene expression.

FIGS. 5 through 13 relate to a specific investigation leading to certain aspects of the present invention. This investigation was performed to test whether decreased expression of KLHL1 in the hind paws of wild-type (WT) mice would render the mice less sensitive to mechanical pain tests. It was theorized that viral delivery of shKLHL1 into wild-type mice hind paws would allow its uptake by L4 DRGNs (spinal cord level 4 DRG neurons), decreasing KLHL1 expression and concomitantly decreasing alpha1H (CaV3.2) calcium channel expression and current density, which would result in decreased DRGN excitability and lower mechanical sensitivity in Von Frey tests. This investigation was expected to determine if the normal painful responses resulting from inoculation with an adenovirus would be dampened in shKLHL1-AAV-injected hind paws compared to control virus-injected paws.

Figure 1B:
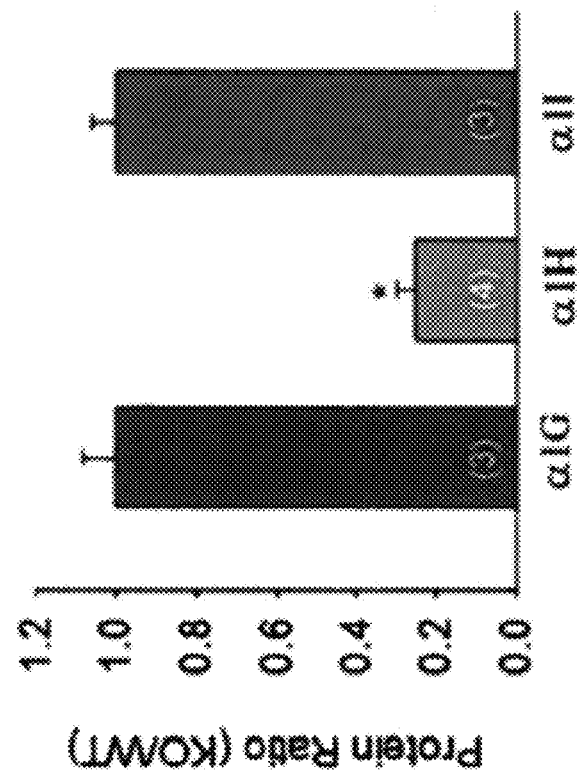
FIGS. 1A and 1B represent expression of T-type alpha1G (α1G), alpha1H (α1H), and alpha1I (α1I) protein in dorsal root ganglia (DRG) from wild-type (WT) and KLHL1 knock-out (KO) mice.
Figure 1A:
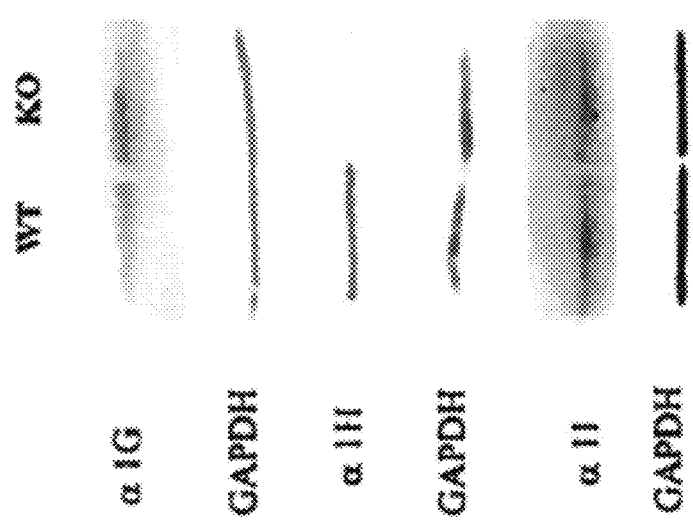
Figure 2A:
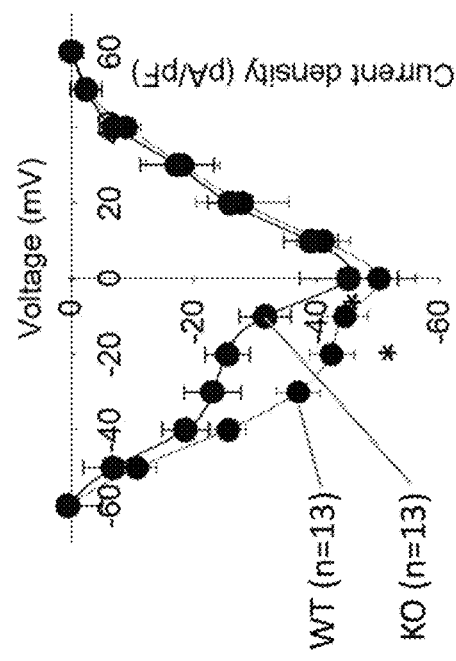
FIGS. 2A through 2D represent that voltage-gated calcium current activity (density in pA/pF) was decreased in KO DRG neurons compared to control wild-type neurons.
Figure 2C:
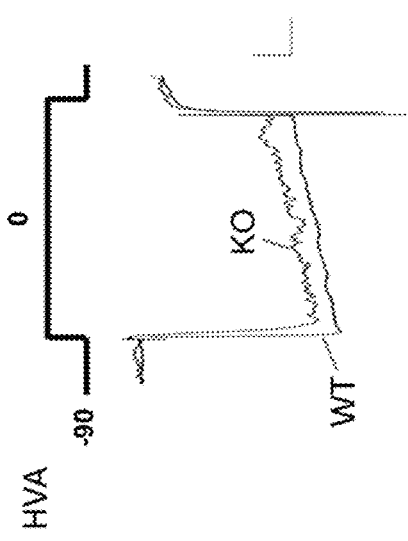
Figure 2B:
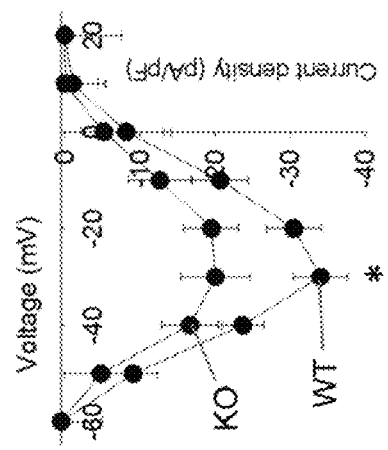
Figure 2D:
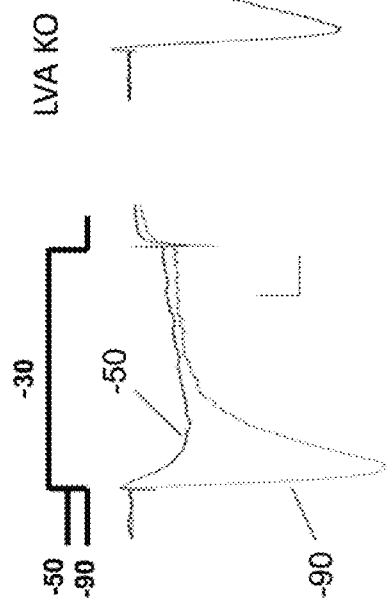
Figure 3A:
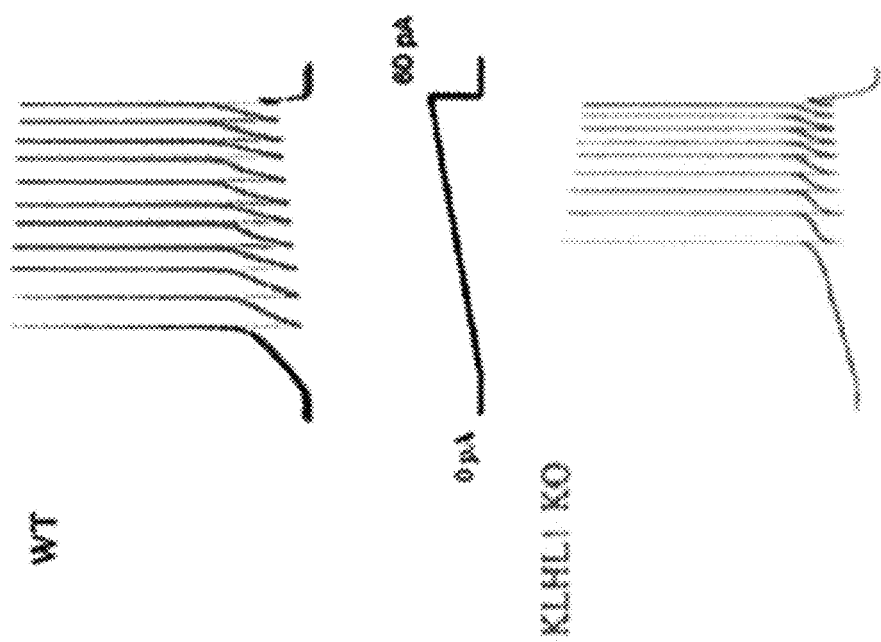
FIGS. 3A and 3B represent current clamp electrophysiology experiments that indicate excitability in KO DRG neurons was decreased.
Figure 3B:
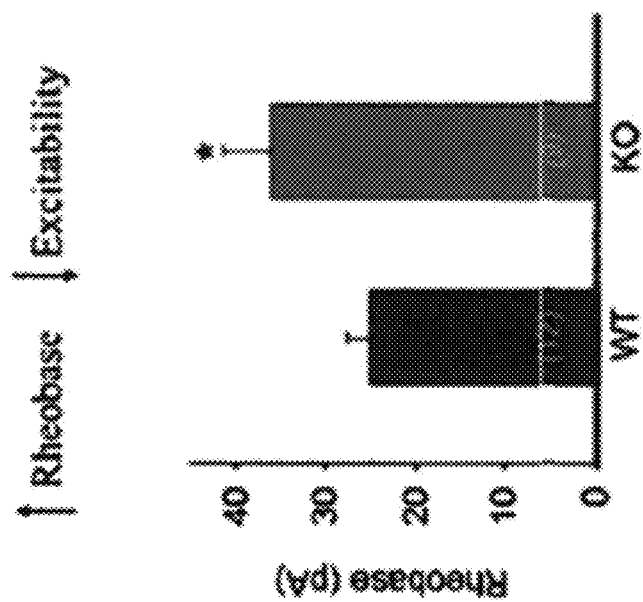
Figure 4C:
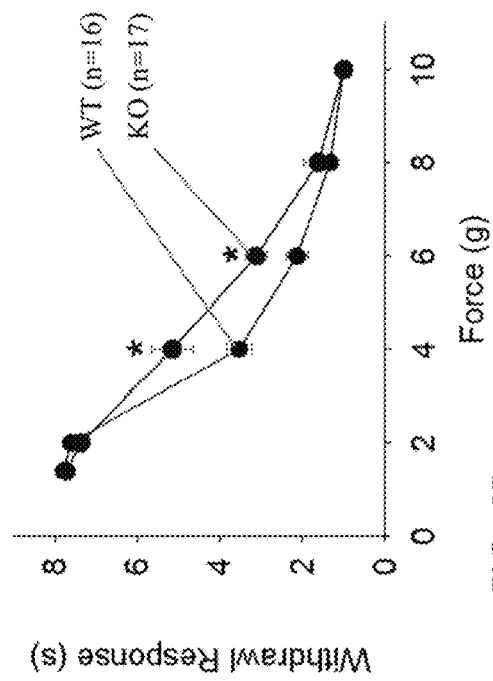
FIGS. 4A through 4D represent behavioral measurements of paw withdrawal time that show KO mice had increased mechanical sensitivity threshold.
Figure 4D:
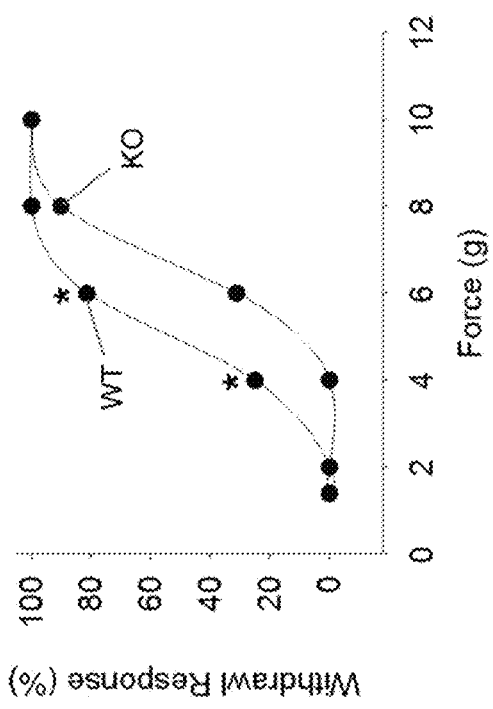
Figure 4A:
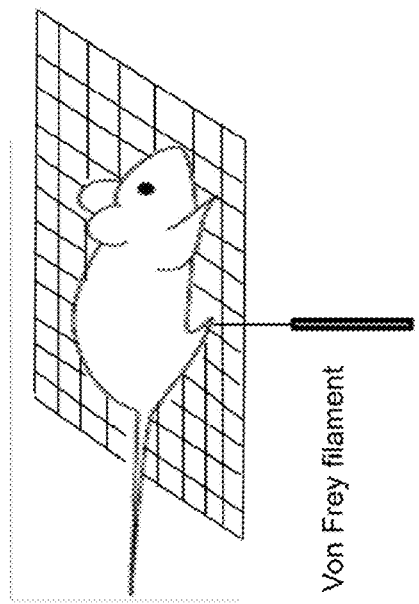
Figure 4B:
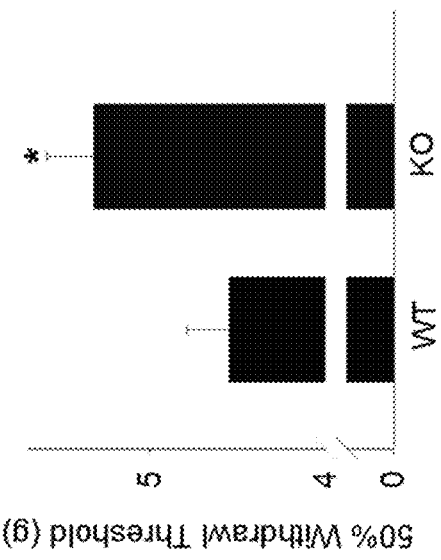
Figure 5:
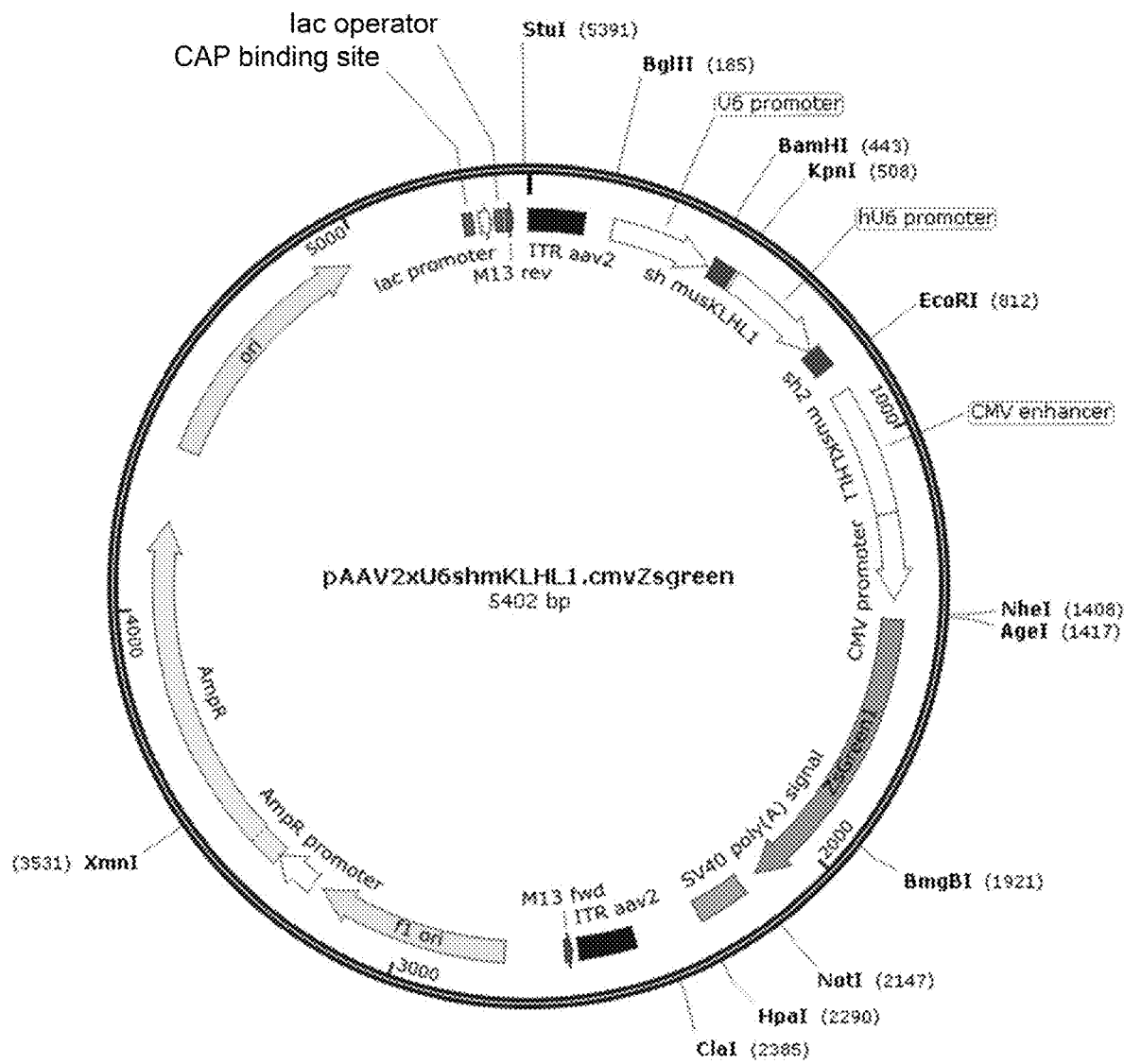
FIG. 5 is a diagram representing a shKLHL1 construct in accordance with aspects of the present invention.

The AAV shuttle vector pZacf-U6-shluc-cmv-Zsgreen was purchased from the University of Pennsylvania gene therapy core. A recombinant adeno-associated virus comprising shKLHL1 was produced for this investigation. Specifically, a DNA fragment with two short hairpin RNA sequences (shRNAs) targeting the KLHL1 gene was synthesized for ligation into pZacf-U6-shluc-Zsgreen while removing the shluc sequence. One of the shRNAs (SEQ ID NO: 1; 5'-GCAGAGTAGATGCAATGACCT-3') was located downstream of a human U6 promoter and the other (SEQ ID NO: 2; 5'-GATAACAACAAAGGAGCTACA-3') was located downstream of another U6 promoter. SEQ ID NO: 1 may start at position 1955 of the *Homo sapiens* KLHL1 sequence (NM 02866.2) and SEQ ID NO: 2 may start at position 2196 of the *Homo sapiens* KLHL1 sequence (NM 02866.2). The fragment had a BamHI restriction site 5' and an EcoRI restriction site 3' for cloning into the shuttle vector. The resultant ligated product was amplified and sequenced for confirmation prior to generation of the recombinant adeno-associated virus. To create the recombinant AAV, this shuttle plasmid, along with a plasmid encoding the rep and cap genes and one encoding helper genes from the adenovirus were co-transfected with polyethylenimine (PEI) into a subclone of HEK293 cells, often referred to as AAV293s. Approximately 66 hours post-transfection, the cells were harvested into 15 ml of lysis buffer, followed by three cycles of freeze thawing before adding benzonase at 50 units/ml for one hour at 37° C. Subsequently the AAV was spun at 4,000 times gravity for 15 minutes at 4° C. before loading onto an iodixanol discontinuous gradient comprised of: 15%, 25%, 40%, and 58% iodixanol layers in Beckman ultraclear quick seal tubes. The tubes were spun at 350000 times gravity for one hour 20 minutes with acceleration set to maximum and the brake set on low. An eighteen-gauge needle was used to extract about three to four milliliters of the interface between the 58% and 40% layers and the buffer was changed and the virus concentrated by centrifugation in a 100 K centrifugal filter. The control AAV consisted of an enhanced green fluorescent protein (EGFP)-expressing AAV (EGFP-AAV). FIG. 5 is a diagram of the shKLHL1 construct produced during this investigation.

Ipsilateral hind paws of wild-type male mice were injected with a control virus expressing only EGFP (EGFP-AAV), whereas the contralateral paws were injected with AAV expressing EGFP and shKLHL1 (shKLHL1-AAV). A total of ten mice were injected in three batches (E1, E2 and E3). E1 (n=3 mice) received daily injections over a period of three days for a total of $5.1 \times 10^{10}$ shKLHL1-AAV vector genomes and $6.6 \times 10^{10}$ EGFP-AAV in the opposite paw (all injections were performed blinded). E2 (n=4) received $3.4 \times 10^{10}$ and $4.4 \times 10^{10}$ shKLHL1-AAV and EGFP-AAV vector genomes, respectively, over a period of two days. E3 (n=4) received $9.0 \times 10^{10}$ shKLHL1-AAV and $9.0 \times 10^{10}$ EGFP-AAV vector genomes over three days. Mice were allowed to recover in observation for four days, checked for any limp or lameness, and confirmed to be healthy. Mice were given pain medication (Buprenorphine, 0.05 mg/kg, s.c.) for the first two days following the last injection. Behavioral tests were performed five days after injection.

Pain sensitivity was tested on the fifth day after injection using Von Frey filaments. Pressure was gently applied to the bottom of both the left or the right paws of each mouse with monofilaments of various forces to determine the withdrawal threshold. The withdrawal response time (in seconds) was recorded for filaments of 1.4 g, 2 g, 4 g, 6 g, and 8 g. If the mouse did not withdraw its paw after eight seconds, the filament was removed because it was assumed that the stimulus was below the withdrawal threshold of the mouse. Each mouse was tested five times on each paw with each filament and averaged. If responses showed a high degree of variability, the procedure was repeated for a total of ten tests per paw on that day. If the mouse was retested, the experimenter waited at least one hour before testing the mouse again so that the mouse would not be sensitized to the filaments. Mice were tested five times prior to injection to establish a baseline response.

Figure 6:
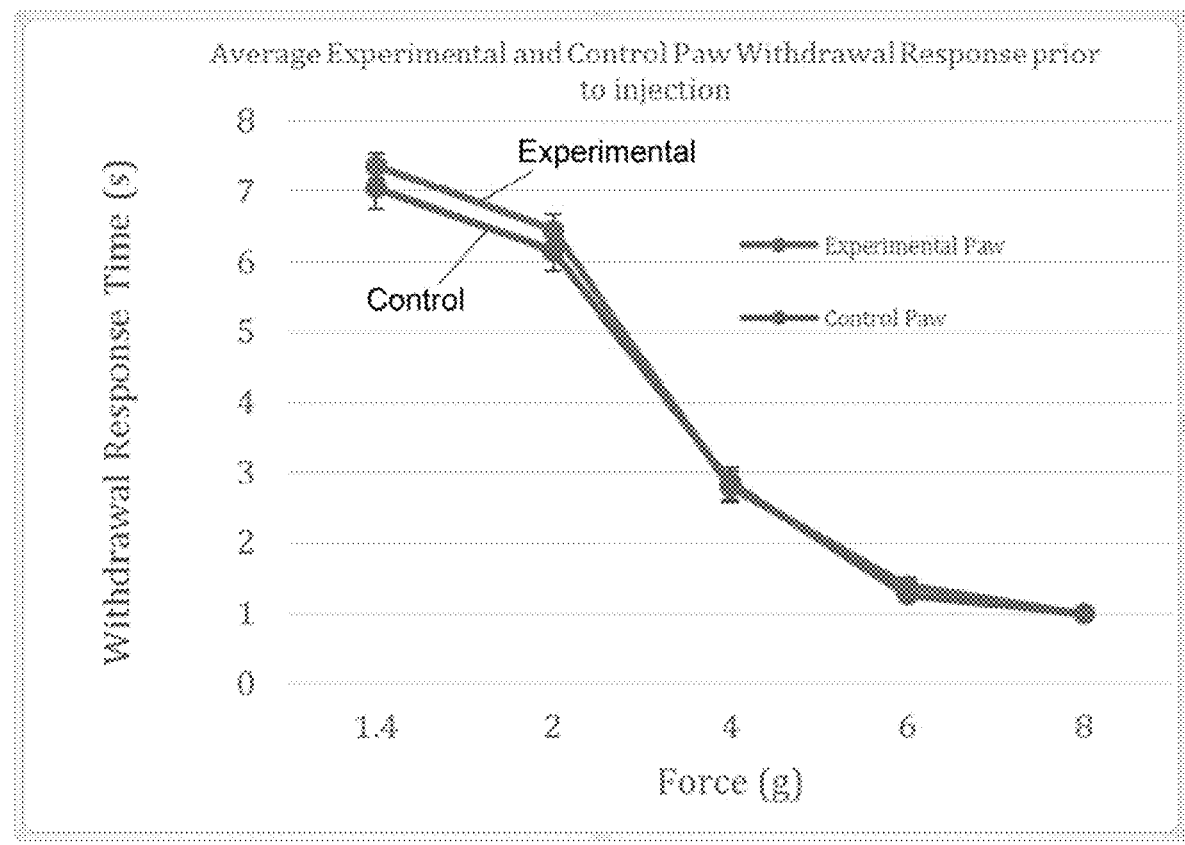
FIG. 6 is a graph representing an average withdrawal time for all mice including control and AAV-injected paws from 1.4 to 8 g filament force prior to injections in the investigation of FIG. 6. There were no differences found between contralateral and ipsilateral paw responses.
Figure 7:
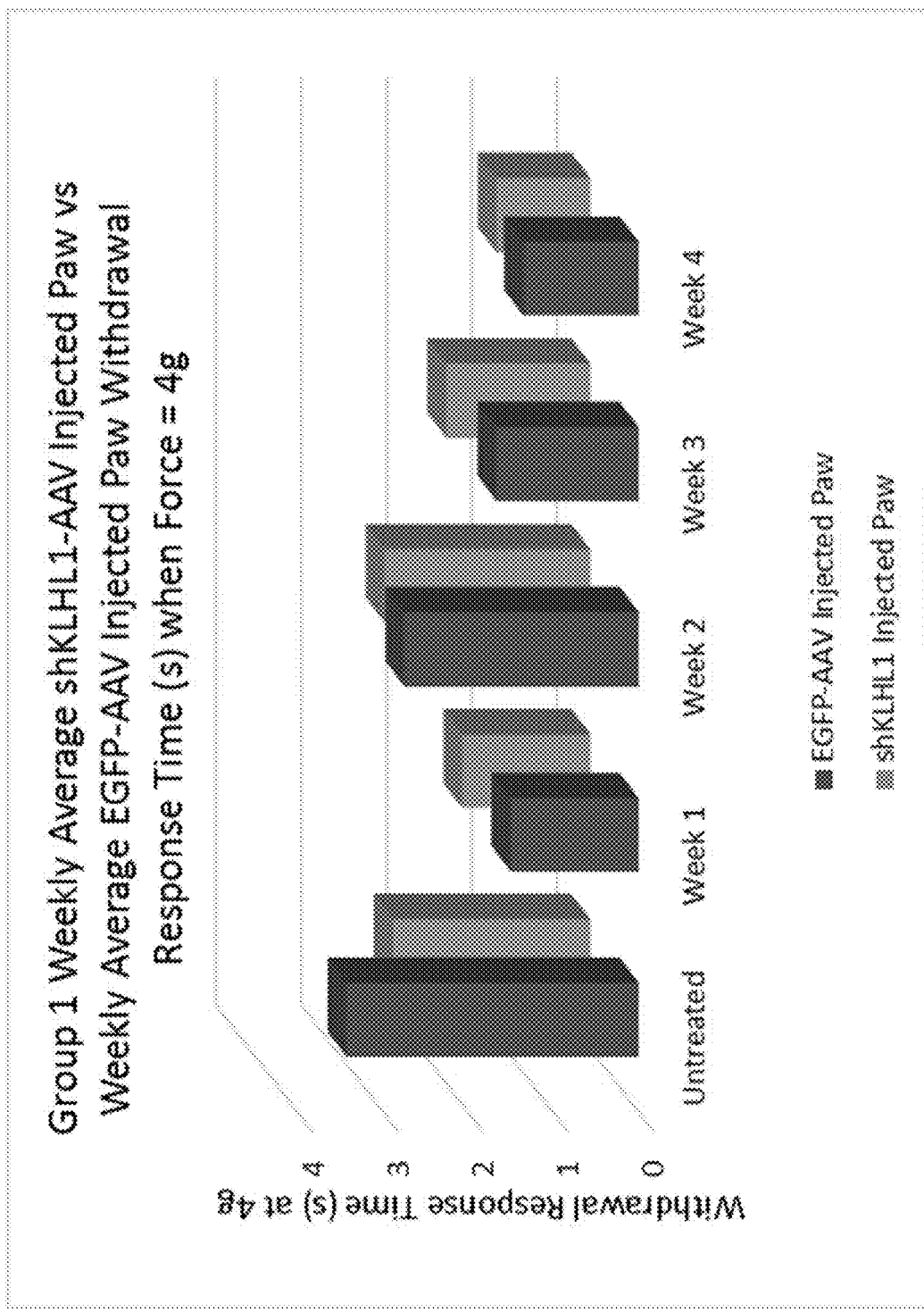
FIGS. 7-12 include graphs representing pain sensitivity results at 4 g of filament pressure (FIGS. 7, 9, and 11) and average withdrawal thresholds over a period of time (FIGS. 8, 10, and 12) from a pain sensitivity investigation. Injection with EGFP-AAV (enhanced green fluorescent protein (EGFP)-expressing adeno-associated virus (AAV)) caused greater pain responses due to the normal side effects of the injection with AAV in the mice paws. In contrast, paws injected with AAV expressing shKLHL1 (shKLHL1-AAV) resulted is less pain sensitivity.
Figure 8:
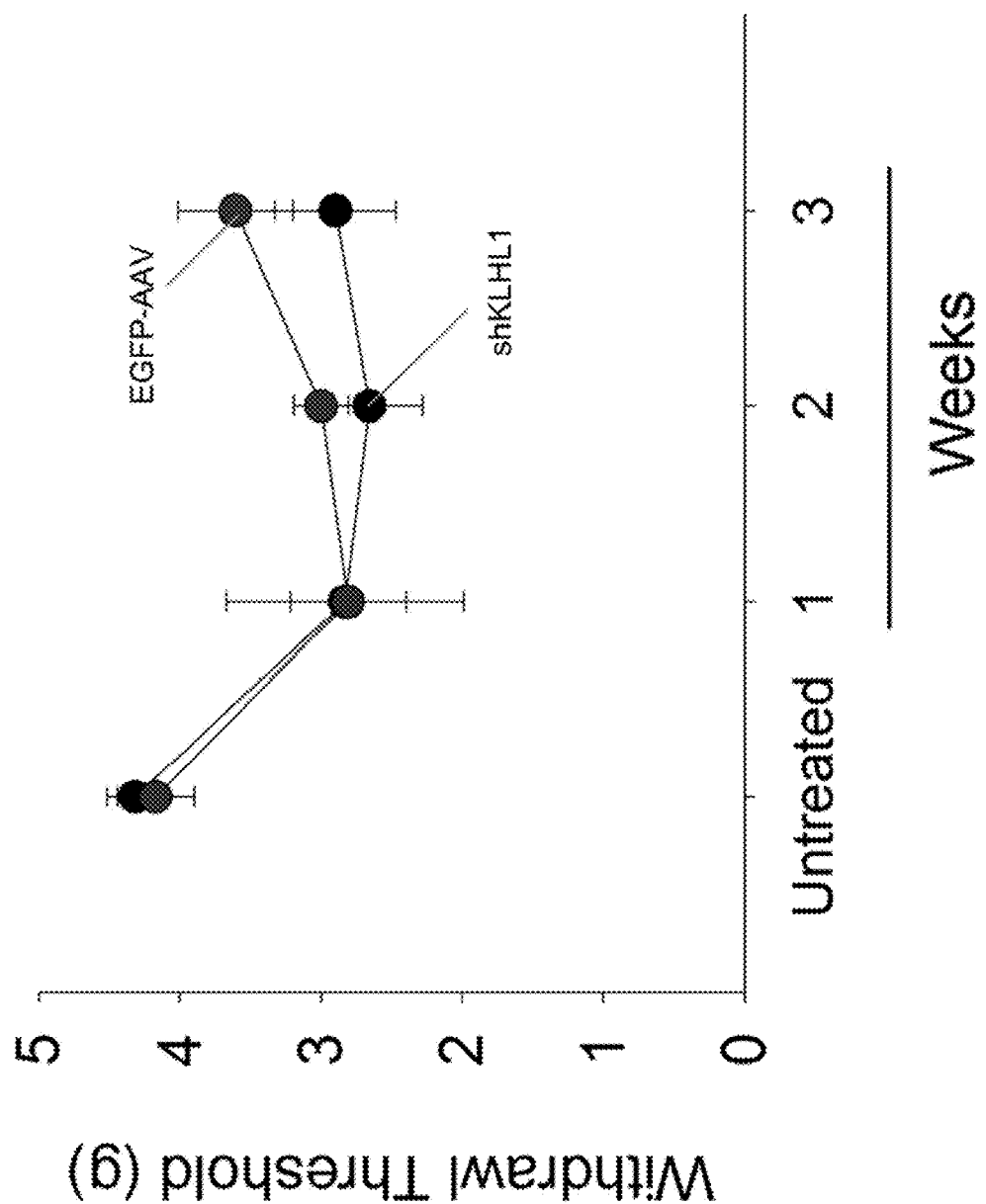
Figure 9:
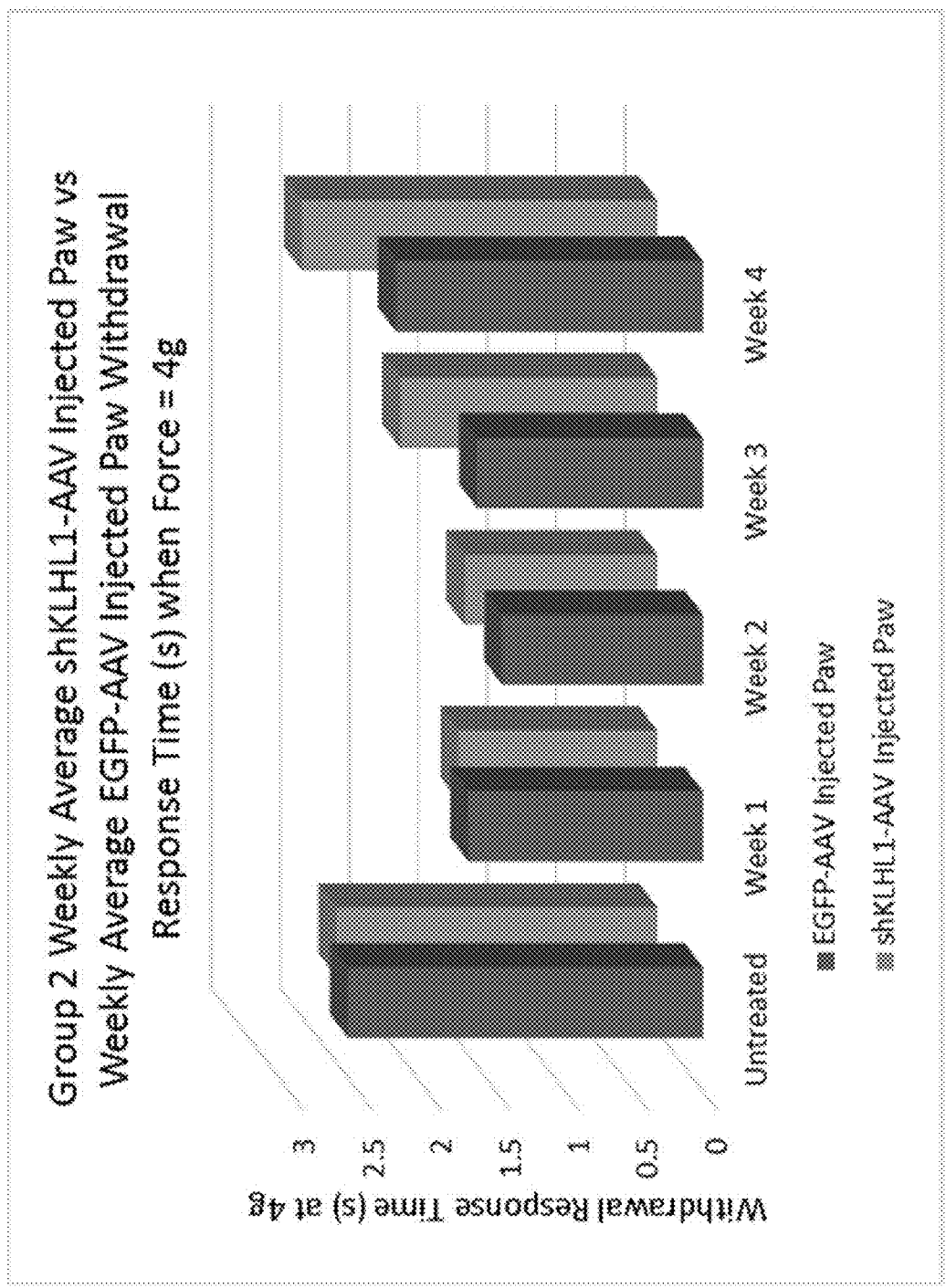
Figure 10:
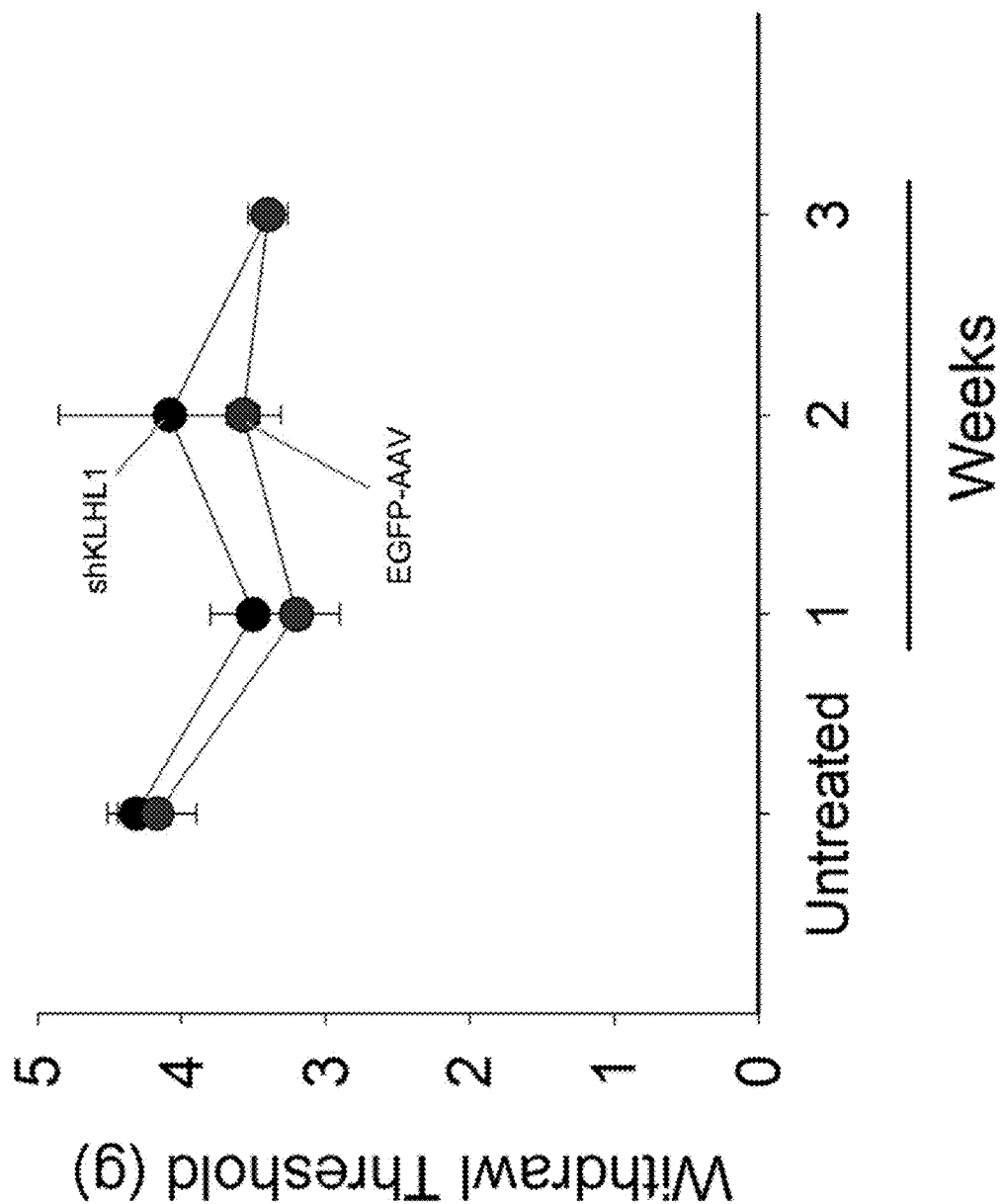
Figure 11:
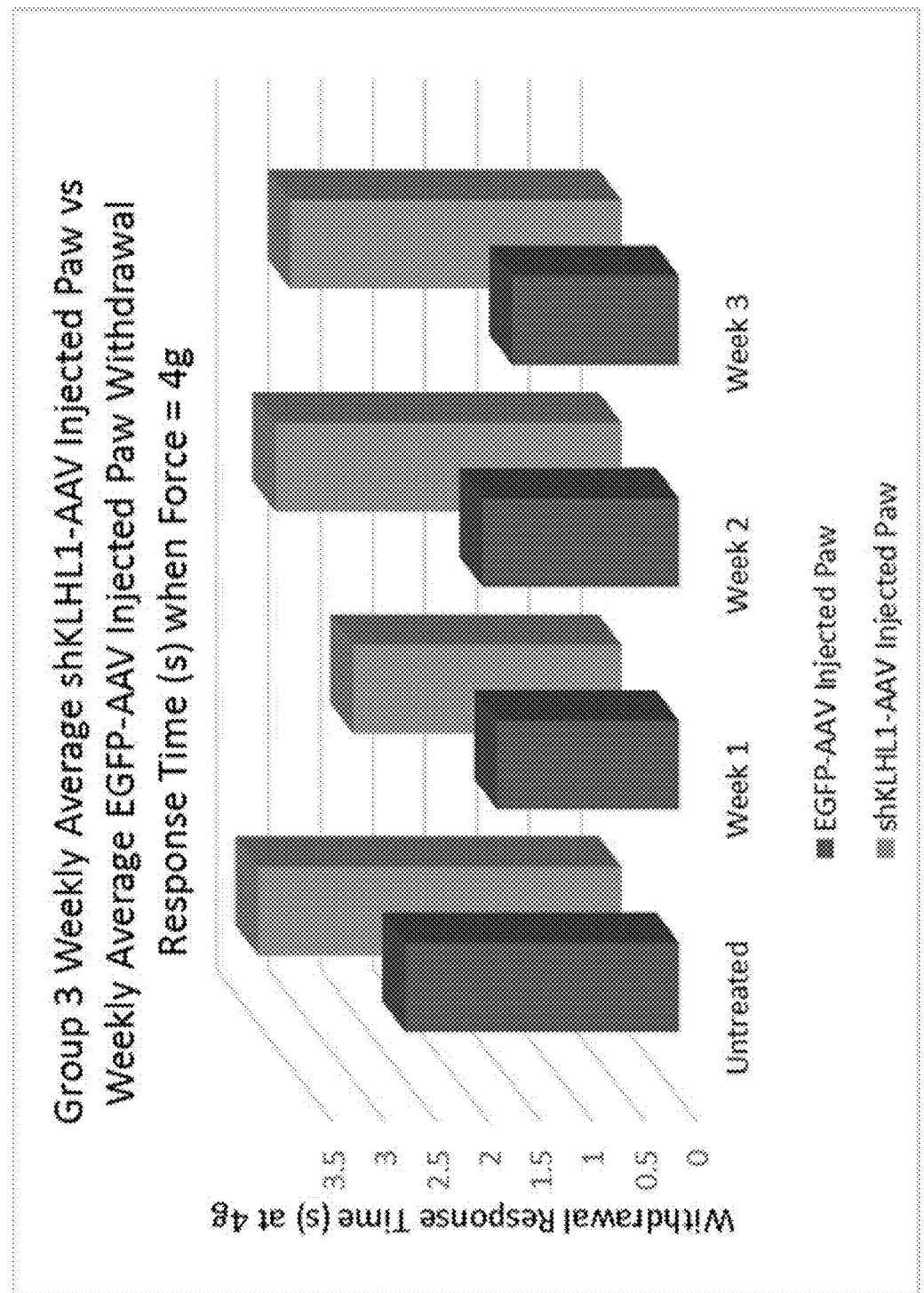
Figure 12:
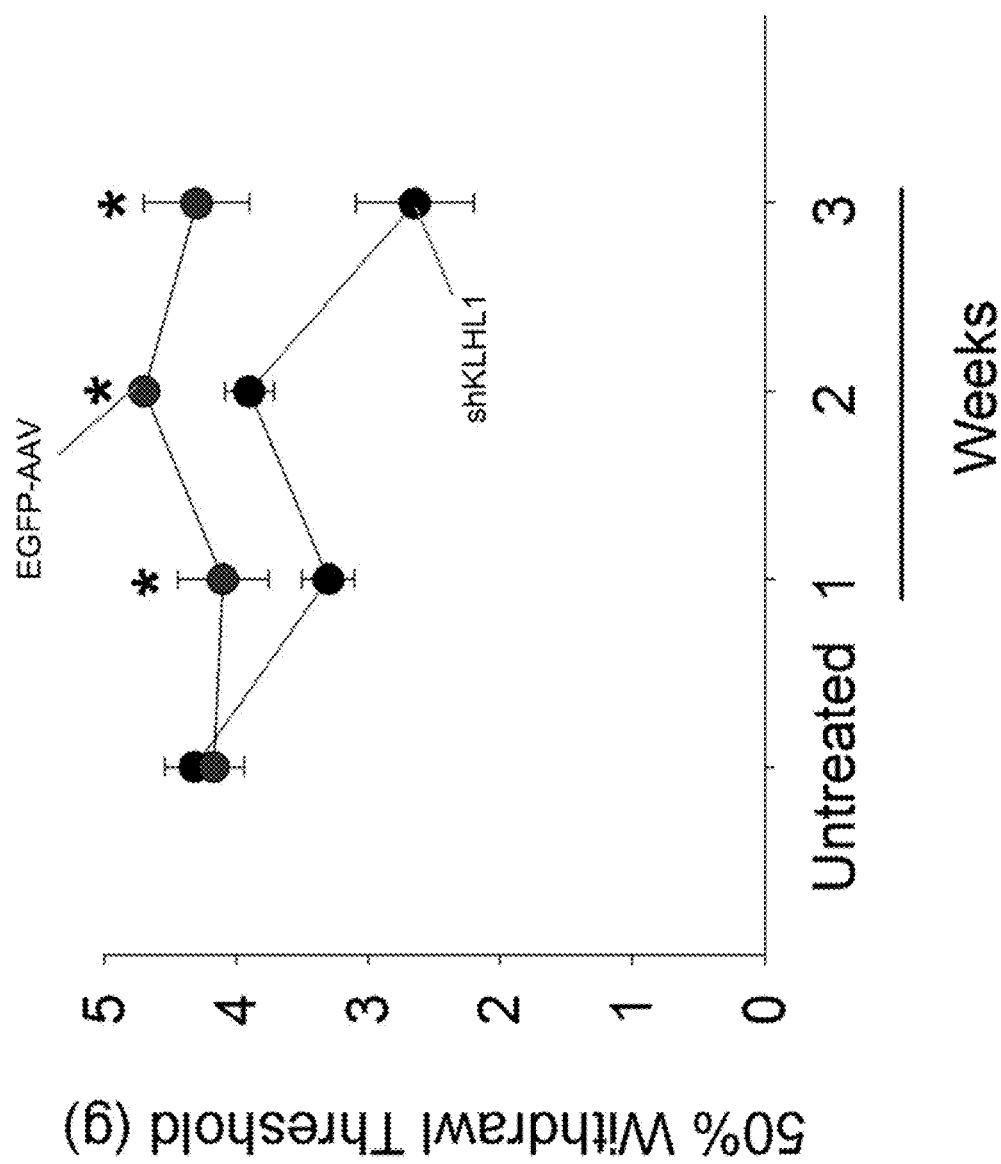

FIG. 6 shows the average withdrawal time for all mice control and shAAV-injected paws from 1.4 g to 8 g filament force prior to injections. There were no differences between contralateral and ipsilateral paw responses. All data reported was of nine mice (except for the western blot represented in FIG. 13, which was pooled from three mice).

After injection, withdrawal responses were measured three to five times a week. Each paw yielded one measurement per day; thus responses were averaged by week, as represented in FIG. 6. Responses after injection were reported as the ratio of the withdrawal response at 4 g on the tested day divided by the corresponding withdrawal response prior to injection. Although injections were done blinded, the differences between shKLHL1-AAV treated paws and control were discernible to the experimenters before un-blinding. Injection with EGFP-AAV caused greater pain responses due to the normal side effects of the injection with AAV in the mice paws. In contrast, paws injected with shKLHL1-AAV resulted is less pain sensitivity in average, with withdrawal values more similar to those seen prior to injection, as represented in FIGS. 7 through 12.

Figure 13:
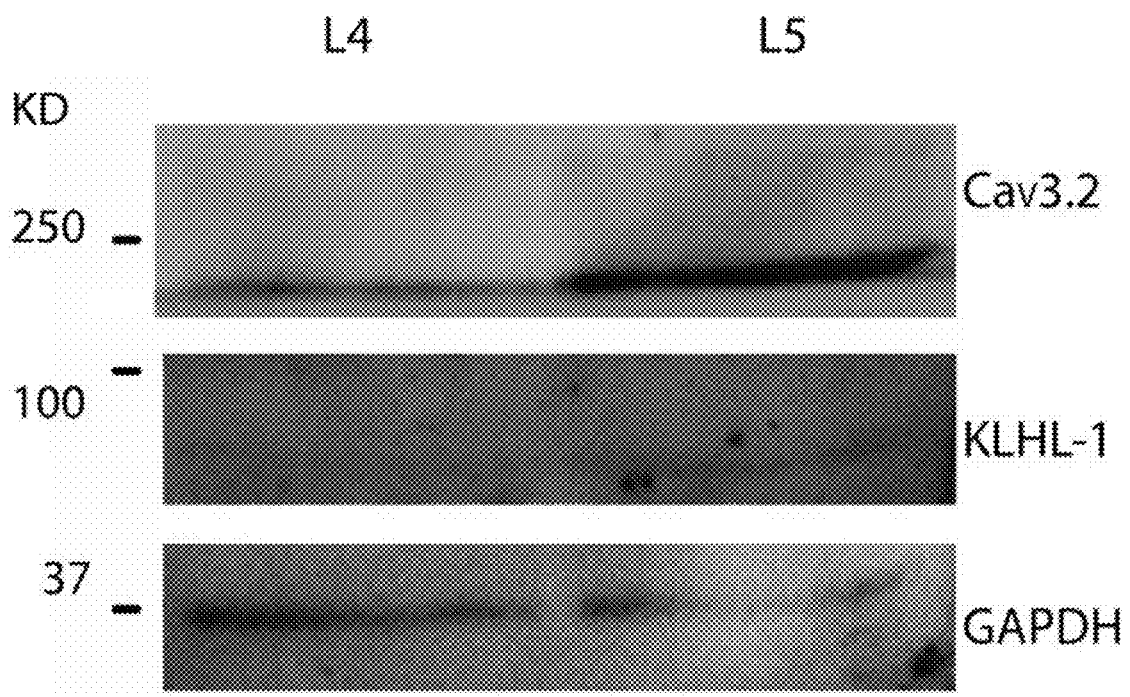
FIG. 13 is western blot results from the pain sensitivity investigation.

The study was unblinded at the end of the behavioral tests. The last tests and dissections were done on day 26 after injection for E1 and E2, and 19 days after injection for E3. The latter was determined to be the optimal day of response after analysis of the E1 and E2 data. The L4 DRG from the control and the experimental side were extracted to analyze the levels of CaV3.2 T-type channel and KLHL1. GAPDH (glyceraldehyde 3-phosphate dehydrogenate) levels were used as internal control. L4 spinal nerves mediate pain sensation of the plantar paw in mice, therefore L5 and/or L3 were extracted as additional controls. DRGs from the same origin were pooled from each group (n=3 ganglia), processed together, and loaded into a single well to reach detection levels. Samples were separated by SDS-PAGE electrophoresis and transferred to a nitrocellulose membrane for western blot processing. Membranes were cut at 50 KD and 150 KD and incubated overnight with primary antibodies against: CaV3.2 ($\alpha$1H) (top portion), KLHL1 (middle), and GAPDH (bottom). As seen in FIG. 13 (L4 and L5 DRG samples from the experimental side of E1), the levels of CaV3.2 and KLHL1 were lower in L4, showing the treatment with shKLHL1-AAV reached the L4 ganglia, exerted its effect lowering the levels of KLHL1, which resulted in reduced CaV3.2 levels, with a decrease in low voltage-activated (LVA) calcium current density and DRG neuron excitability, leading to more resistance to pain on the shKLHL1-AAV injected limbs.

In view of the above data, it was determined that down-regulation of KLHL1 expression leads to decreased expression of CaV3.2, decreased LVA calcium current density, and decreased neuronal excitability thus decreasing mechanical pain sensitivity in wild-type mice.

Figure 14:
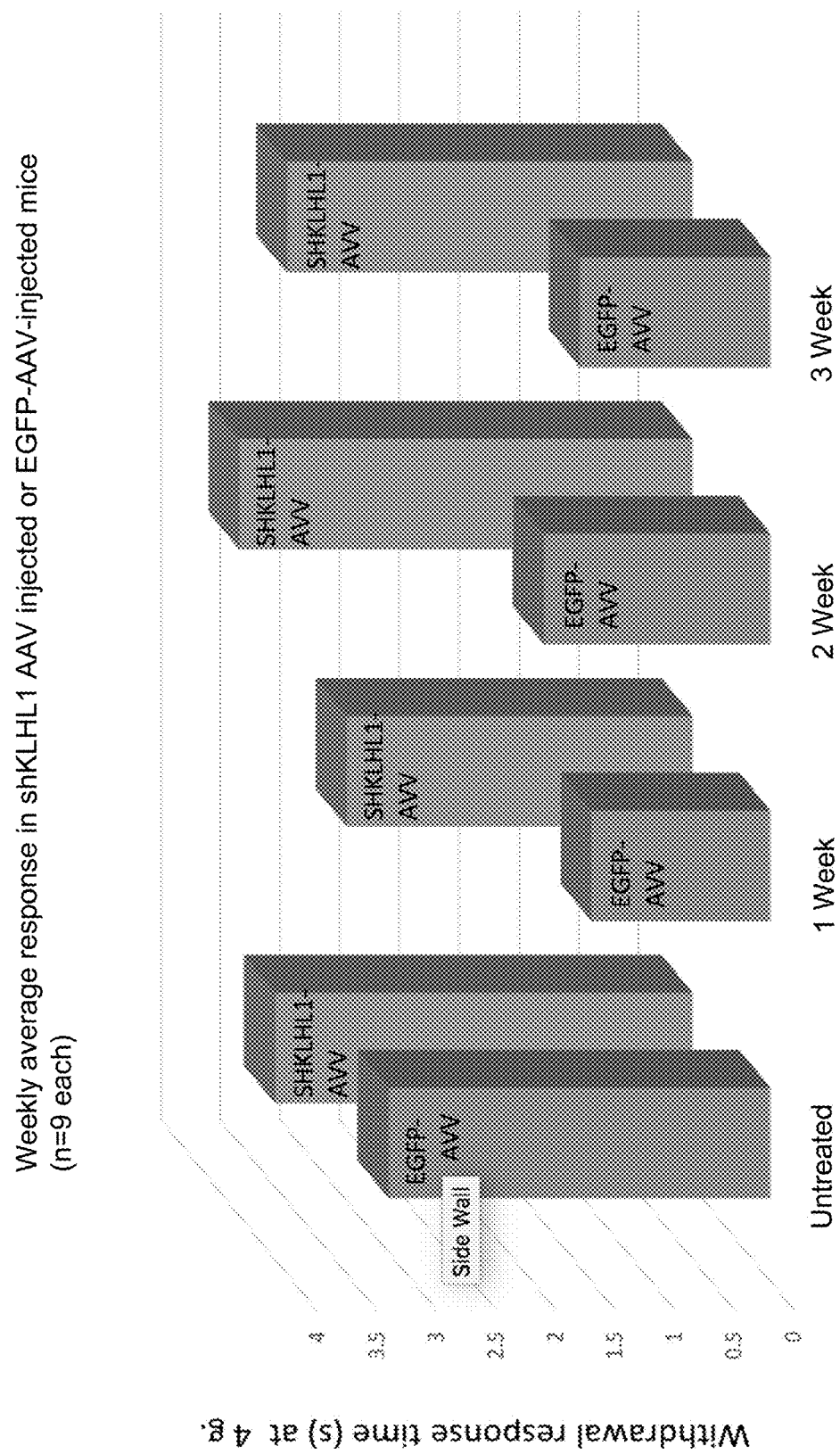
FIG. 14-15 (withdrawal response time at 4 g, and withdrawal threshold, respectively) represent the analysis of a second round of experiments performed with a cohort of 8 mice each (control and shKLHL1-injected) at the high viral titer load of 9×10^10, to confirm the prior data on the efficacy of the higher titer concentration and the reproducibility of the data. The data confirms that delivery of shKLHL1 results in reduced pain sensitivity compared to EGFP-injected mice.
Figure 15:
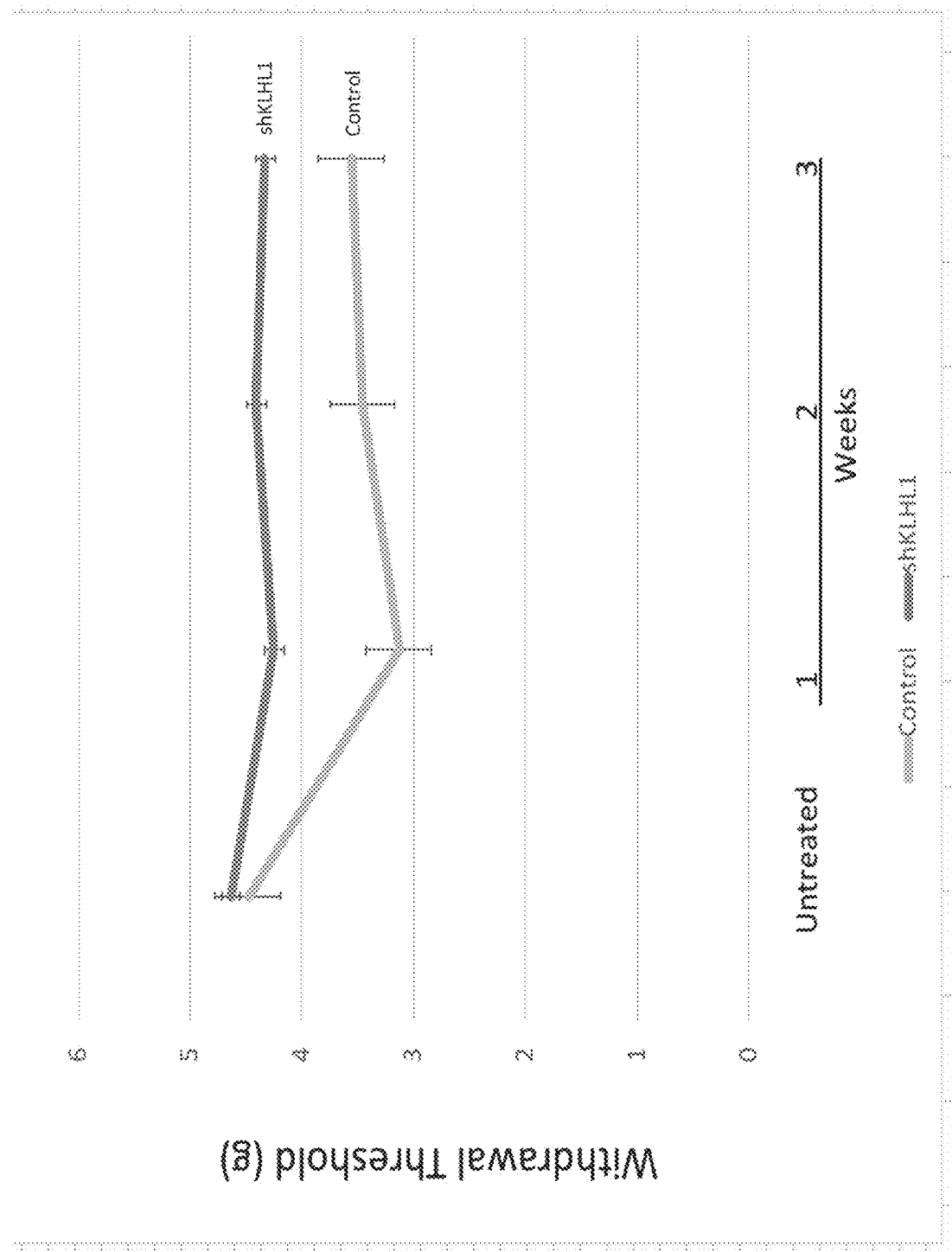

A second round of experiments to verify the reproducibility and efficacy of high viral load dose was performed by injecting mice a cohort of 8 mice for each group with a high titer trial of $9.0 \times 10^{10}$ AVV-shKLHL1 or $8.5 \times 10^{10}$ AVV-EGFP vector genomes over 2 days. The behavioral measurements were performed under blinded conditions, as in prior tests. This treatment (FIG. 14) induced significant differences in mechanical threshold values in shKLHL1-injected mice after 1 week, but not prior to treatment: untreated: EGFP-AAV (3.2±0.2 g); shKLHL1-AAV-1 (3.5±0.3 g) (n=8, p=0.2), Week 1: EGFP-AAV (1.5±0.2 g); shKLHL1-AAV-1 (2.9±0.1 g) (n=8, p=0.0008). Week 2: EGFP-AAV (1.9±0.2 g); shKLHL1-AAV-1 (3.8±0.3 g) (n=8, p=0.0002). Week 3: EGFP-AAV (1.6±0.4 g); shKLHL1-AAV-1 (3.4±0.4 g) (n=8, p=0.004) (FIG. 14). The data is also represented in FIG. 15 as the calculated 50% withdrawal threshold (in g). This experiment confirms that delivery of $9.0 \times 10^{10}$ AVV-shKLHL1 results in reduced pain sensitivity compared to mice injected with AVV-EGFP.

On the basis of the above, it was concluded that neuronal excitability can be controlled by a method that includes administration of a compound or composition configured for controlling, modulating, increasing, or decreasing KLHL1 levels in a subject. According to this aspect of the invention, an shRNA molecule engineered to target a KLHL1 gene in a subject is provided in order to control or modulate KLHL1 levels within the subject. As known in the art, shRNA may be used to silence target gene expression via RNA interference (RNAi). By modulating KLHL1 gene expression and thereby controlling KLHL1 levels, the neuronal excitability may be indirectly controlled. The shRNA may be administered to the subject by any means known in the art. Exemplary delivery means include, but are not limited to, local injection of a plasmid encoding the shRNA and viral vector delivery, such as with an adeno-associated virus (AAV). Although the above example modulates KLHL1 gene expression to control KLHL1 levels, it is within the scope of the invention that a composition or compound may modulate KLHL1 levels by means unrelated to gene expression. The shRNA may be delivered by any means, including but not limited to delivery via liposomes, PEI, and viral methods. Liposomal delivery of siRNA has been reported in Schultheis et al., First-in-human phase I study of the liposomal RNA interference therapeutic Atu027 in patients with advanced solid tumors, J Clin Oncol. 2014 Dec. 20; 32(36): 4141-8. PMID: 25403217), incorporated herein by reference.

Various disorders have been previously reported to be treatable through conventional methods that directly modulate T-type channel activity by administering drugs that generally include a T-type calcium channel inhibitor as an effective ingredient. It is believed that such disorders may also be treatable with the methods noted above, including indirectly modulating T-type channel activity by administering drugs that modulate KLHL1 levels. Nonlimiting applications include local injection into target areas of the subject to treat neuropathic pain (injected into pain sensitive areas or a nerve), intrathecal administration (injection or pump delivery system) for treatment of intractable cancer pain in subjects no longer responsive to opioid treatment, direct injection into inoperable tumors to provide tumor growth control in the brain, local injection into target areas to treat epilepsy, direct injection into the adrenal gland to treat adrenal gland hypo-secretory diseases, the treatment of irritable bowl syndrome, fibromyalgia, and direct injection into the prostate in order to reduce neuroendocrine differentiation of prostate epithelial cells in prostate cancer. In addition to the above example applications, it may be possible to use over-expression of KLHL1 using a viral delivery system to treat Alzheimer's disease (increasing neuronal activity of hippocampal neurons to counteract neuronal loss).

The dose of the pharmaceutical administered to a subject, particularly a human, in the context of the present invention, should be sufficient to effect a therapeutic response in the animal over a reasonable time frame. Those of ordinary skill in the art will recognize that dosage will depend upon a variety of factors including the condition of the subject, the body weight of the subject, the nature and extent of the symptoms, the kind of concurrent treatment, the frequency of treatment, etc. The size of the dose also will be determined by the route, timing, and frequency of administration as well as the existence, nature, and extent of any adverse side effects that might accompany the administration of the pharmaceutical and the desired physiological effect. Appropriate dosing may be determined empirically from clinical trials, starting with doses that have established safety profiles when used for other applications.

In view of the above, it is within the scope of the invention that compositions or pharmaceuticals may be produced that comprise a KLHL1 modulator for treating pain and other conditions. Furthermore, it is within the scope of the invention that such compositions or pharmaceuticals may be screened for by investigating the effect of various compounds, compositions, existing pharmaceuticals, etc., on KLHL1 levels, KLHL1 gene expression, and/or T-type calcium channel activity. Examples of KLHL1 modulators include but are not limited to, promoter sequence binding proteins (activators or repressors of KLHL1 gene expression), molecules that disrupt the KLHL1-alpha1H channel-actin interaction, etc.

The methods, compositions, compounds, etc., disclosed herein have been shown to provide for control over the function of calcium channels. That is, manipulation of KLHL1 levels provides an indirect alternative for ion channel modulation. It is believed that targeting of KLHL1, a T-type channel modulator, rather than direct targeting of T-type channels has the potential to avoid possible side effects of direct T-channel targeting.

While the invention has been described in terms of specific embodiments, it is apparent that other forms could be adopted by one skilled in the art. For example, various compounds could be used to modulate KLHL1 levels, processing parameters such as dosages and durations could be modified, and materials and processes/methods other than those noted could be used. Therefore, the scope of the invention is to be limited only by the following claims.

The invention claimed is:

1. A method of modulating a kelch-like protein 1 (KLHL1) level in a subject, the method comprising the steps of:
   providing a single adeno-associated virus vector encoding two small hairpin RNA (shRNA) sequences that target a KLHL1 gene; and
   administering the adeno-associated virus vector encoding the shRNA sequences to the subject in an amount sufficient to modulate KLHL1 gene expression;
   wherein the KLHL1 level directly effects current activity in T-type calcium channels and the adeno-associated virus vector is administered to the subject in an amount sufficient to modulate the current activity in the T-type calcium channels; and
   wherein the current activity in the T-type calcium channels is modulated to decrease expression of CaV3.2, decrease LVA calcium current density, and decrease neuronal excitability in order to treat pain.

2. The method of claim 1, wherein the current activity in the T-type calcium channels is modulated to treat intractable cancer pain, control tumor growth in the brain, treat epilepsy, treat adrenal gland hypo-secretory diseases, treat of irritable bowel syndrome, treat fibromyalgia, or reduce neuroendocrine differentiation of prostate epithelial cells in prostate cancer.

3. The method of claim 2, wherein each shRNA sequence has a sequence as set forth in SEQ ID NO: 1 or a sequence as set forth in SEQ ID NO: 2.

4. A method of modulating current activity in T-type calcium channels in a subject, the method comprising the steps of:
   providing a single adeno-associated virus vector encoding two small hairpin RNA (shRNA) sequences that target a ketch-like protein 1 (KLHL1) gene; and
   administering the adeno-associated virus vector encoding the shRNA sequences to the subject in an amount sufficient to modulate KLHL1 gene expression, wherein the KLHL1 level directly effects current activity in T-type calcium channels;
   wherein the adeno-associated virus vector is administered to the subject in a therapeutic amount to treat pain, and the current activity in the T-type calcium channels is modulated to decrease expression of CaV3.2, decrease LVA calcium current density, and decrease neuronal excitability.

5. The method of claim 4, wherein the current activity in the T-type calcium channels is modulated to to treat intractable cancer pain, control tumor growth in the brain, treat epilepsy, treat adrenal gland hypo-secretory diseases, treat of irritable bowel syndrome, treat fibromyalgia, or reduce neuroendocrine differentiation of prostate epithelial cells in prostate cancer.

6. A method of modulating a kelch-like protein 1 (KLHL1) level in a subject, the method comprising the steps of:
   providing a single adeno-associated virus vector encoding two small hairpin RNA (shRNA) sequences that target a KLHL1 gene; and
   administering the adeno-associated virus vector encoding the shRNA sequences to the subject in an amount sufficient to modulate KLHL1 gene expression;
   wherein the KLHL1 level directly effects current activity in T-type calcium channels and the adeno-associated virus vector is administered to the subject in an amount sufficient to modulate the current activity in the T-type calcium channels; and
   wherein the current activity in the T-type calcium channels is modulated to decrease expression of CaV3.2 and decrease LVA calcium current density to treat intractable cancer pain, control tumor growth in the brain, treat epilepsy, treat adrenal gland hypo-secretory diseases, treat of irritable bowel syndrome, treat fibromyalgia, or reduce neuroendocrine differentiation of prostate epithelial cells in prostate cancer.

7. The method of claim 5, wherein each shRNA sequence has a sequence as set forth in SEQ ID NO: 1 or a sequence as set forth in SEQ ID NO: 2.

8. The method of claim 6, wherein each shRNA sequence has a sequence as set forth in SEQ ID NO: 1 or a sequence as set forth in SEQ ID NO: 2.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gcagagtaga tgcaatgacc t                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gataacaaca aaggagctac a                                              21